(12) United States Patent
Wartelle et al.

(10) Patent No.: US 6,342,072 B1
(45) Date of Patent: Jan. 29, 2002

(54) ARTIFICIAL HEART CAPABLE OF BEING WHOLLY IMPLANTED

(75) Inventors: Claude André Wartelle, Gouvieux; Alain Marcel Denamur, Senlis, both of (FR)

(73) Assignee: Centre Technique des Industries Mecaniques, Senlis (FR)

( * ) Notice: Subject to any disclaimer, the term of this patent is extended or adjusted under 35 U.S.C. 154(b) by 0 days.

(21) Appl. No.: 09/380,933

(22) PCT Filed: Mar. 18, 1998

(86) PCT No.: PCT/FR98/00544

§ 371 Date: Sep. 10, 1999

§ 102(e) Date: Sep. 10, 1999

(87) PCT Pub. No.: WO98/41247

PCT Pub. Date: Sep. 24, 1998

(30) Foreign Application Priority Data

Mar. 19, 1997 (FR) ............................................. 97 03349

(51) Int. Cl.[7] ............................................... A61M 1/10
(52) U.S. Cl. ........................................ 623/3.2; 417/412
(58) Field of Search ............................... 623/3.16, 3.17, 623/3.18, 3.19, 3.2, 2.21, 3.22; 600/17, 18, 16; 417/412, 534, 521

(56) References Cited

U.S. PATENT DOCUMENTS

| 4,058,857 | A | | 11/1977 | Runge et al. |
| 4,750,903 | A | | 6/1988 | Cheng |
| 5,135,539 | A | * | 8/1992 | Carpentier ..................... 623/3 |
| 5,976,184 | A | * | 11/1999 | Buecherl et al. ............... 623/3 |

FOREIGN PATENT DOCUMENTS

FR          2 625 903          7/1989

* cited by examiner

*Primary Examiner*—Bruce Snow
(74) *Attorney, Agent, or Firm*—Hoffmann & Baron, LLP (57) ABSTRACT

The invention concerns an artificial heart capable of being wholly implanted including in a single-piece module (2) two independent ventricular chambers (22G, 22D) each provided with two orifices (11G, 11D, 12G, 12D) equipped with a valve for respectively releasing and pumping blood. The volume of each chamber (22G, 22D) is variable by means of a mobile membrane (17, 18) constituting a wall of the chamber (22G, 22D) and hydraulically actuated by a fluid driven by an actuator comprising a motor and a volumetric pump. The ventricular chambers (22G, 22D) are arranged so as to form an upside-down V, between whose branches are arranged the actuators and the space (37) for the actuating fluid. The chambers (22G, 22D) include on the outside convex walls (7G, 7D) the releasing and pumping orifices (11G, 11D, 12G, 12D).

7 Claims, 10 Drawing Sheets

ARTIFICIAL HEART CAPABLE OF BEING WHOLLY IMPLANTED

BACKGROUND OF THE INVENTION

1. Field of the Invention
2. Prior Art

The invention relates to an artificial heart capable of being wholly implanted.

Document EP-A-0 079 373 discloses a complete cardiac prosthesis whose ventricular chambers are actuated by pumps separate from the heart itself. This results in substantial load losses, a large volume of pumping oil and a certain bulkiness of the system.

A significant improvement has been obtained by virtue of the architecture described in document FR-A-2 625 903. This architecture, which is the basis of the present invention, is characterized by a one-piece module housing two independent ventricular chambers each provided with two orifices fitted with valves respectively for the expulsion and admission of blood, each chamber having a variable volume by virtue of a movable membrane which forms a wall of the chamber and is hydraulically operated by a fluid driven by an actuator comprising a motor and a volumetric pump integrated within the body.

In the artificial heart described in the above document—just as in the one described in EP-A-0 079 373—the ventricular chambers are face to face forming a V-shape with the point at the bottom, and between the branches of which are arranged the expulsion and admission orifices for attachment to the natural organs. The exterior of the V is reserved for the hydraulic chambers that actuate the membranes and for the motorized pumps, in an appendicular position.

U.S. Pat. No. 4,750,903 states that it is not possible to miniaturize a membrane type of heart sufficiently to make it truly implantable and proposes a different, pocket-type heart.

In spite of its interest, this artificial heart can still be improved both from the point of view of compactness and also by the reduction of hydraulic pressure losses on the actuating side. Such is the object of the present invention.

The present invention distinguishes from the above by an architecture which runs counter to the orthodox approaches. It is essentially characterized in that the ventricular chambers are arranged so as to form an upside down V, i.e. with the point at the top, and between the branches of which are arranged the above-mentioned actuators and the space intended for the actuating fluid.

Thanks to this revolutionary architecture, the heart's overall volume can be reduced by obviating the need for a collector which, in the previous architecture, has to pass round the connector flange between the ventricular chamber and the actuating chamber to bring the actuating fluid thereto. In the proposed new architecture, the positions of the ventricular and actuating chambers have been exchanged, the centrally mounted actuators expulse the fluid directly into the actuating chambers; load losses are reduced, and the total quantity of actuating fluid required is lower and easy to confine to the center of the heart. Moreover, by contrast with the known architecture, it is no longer necessary to provide a protective strainer for the supple reservoir bag which encloses the operating oil and which was up till now provided to prevent an untimely aspiration of the bag by the pumps.

Another advantage of the new heart is that all the surfaces in contact with blood can easily be made hemocompatible; indeed, apart from the hemocompatible membrane known in the state of the art, all the other surfaces intended to be in contact with blood are advantageously made of titanium, well known for its excellent hemocompatibility.

The ventricular chambers of the wholly implantable heart according to the invention externally present curved walls on which are arranged the expulsion and admission orifices.

According to a very advantageous characteristic of the invention, the actuators are arranged substantially within the zone of the median symmetry plane of the V formed by the chambers, their axes approximately forming a right angle, the motors being located outside the right angle and the pumps inside the right angle.

According to the invention, the artificial heart comprises a central body which provides one or a plurality of the following functions:

- left and right ventricles containing the membrane actuating fluid
- actuating fluid reservoir
- support and positioning for the actuator motor pump units
- pump fluid collector
- pump distributor
- membrane mount
- pressure and position sensor mount
- mount for fixing and sealing the supple bag fluid reservoir
- electronic circuit board mount for the motor drive circuit, sensor conditioning electronics and medical control and regulation electronics
- mount for the external connection electrical cord
- mount for the ventricular caps and the external body shell.

Advantageously, the central body—which is preferably made of plastics material—supports the actuators and defines two cups inclined to form a V-shape, the rim of which retains the movable membrane surmounted by the above-mentioned curved wall made of titanium, each cup forming with the membrane an actuating chamber supplied with oil by the actuators, whose pump is interposed between the internal space of the above chamber and an oil confinement space formed in and around the central body and limited by a supple bag reservoir, the entire assembly being enclosed in a rigid titanium body shell.

The central portion fitted with the actuating units, sensors, membranes and the electronics immerged in the fluid confined in a supple reservoir forms an autonomous and intelligent actuating system.

The biological part, formed by a shell and two ventricular caps with the connection pipes supporting the valves, completely surrounds the actuator and is made of microballed titanium sheeting to ensure compatibility with blood and tissues.

Some of the characteristics and advantages described in document FR-A-2 625 903 are or can be adopted in the novel architecture of the invention:

- separation of the blood zones and zones serving for actuation and regulation
- electrohydraulic actuation provided by a brushless direct current motor and a volumetric pump with internal gears and radial expulsion
- use of a complex membrane ensuring compatibility with blood and the actuating fluid
- independent flowrates for the right and left ventricles
- connection between the prosthesis and the auricles by a spectacle-shaped quick connector
- hemocompatibility and biocompatibility ensured by porous surfaces made of biocompatible materials flowrate regulation through speed variation of the electric motors controlled by a digital electronic system reproducing in real time the behavior of the cardiac muscle from measurements of the ventricular pressure and volumes expulsed by the volumetric pumps.

Other characteristics and advantages of the invention shall become more apparent from reading the description of the preferred embodiment, given with reference to the appended drawings in which.

Figure 1:
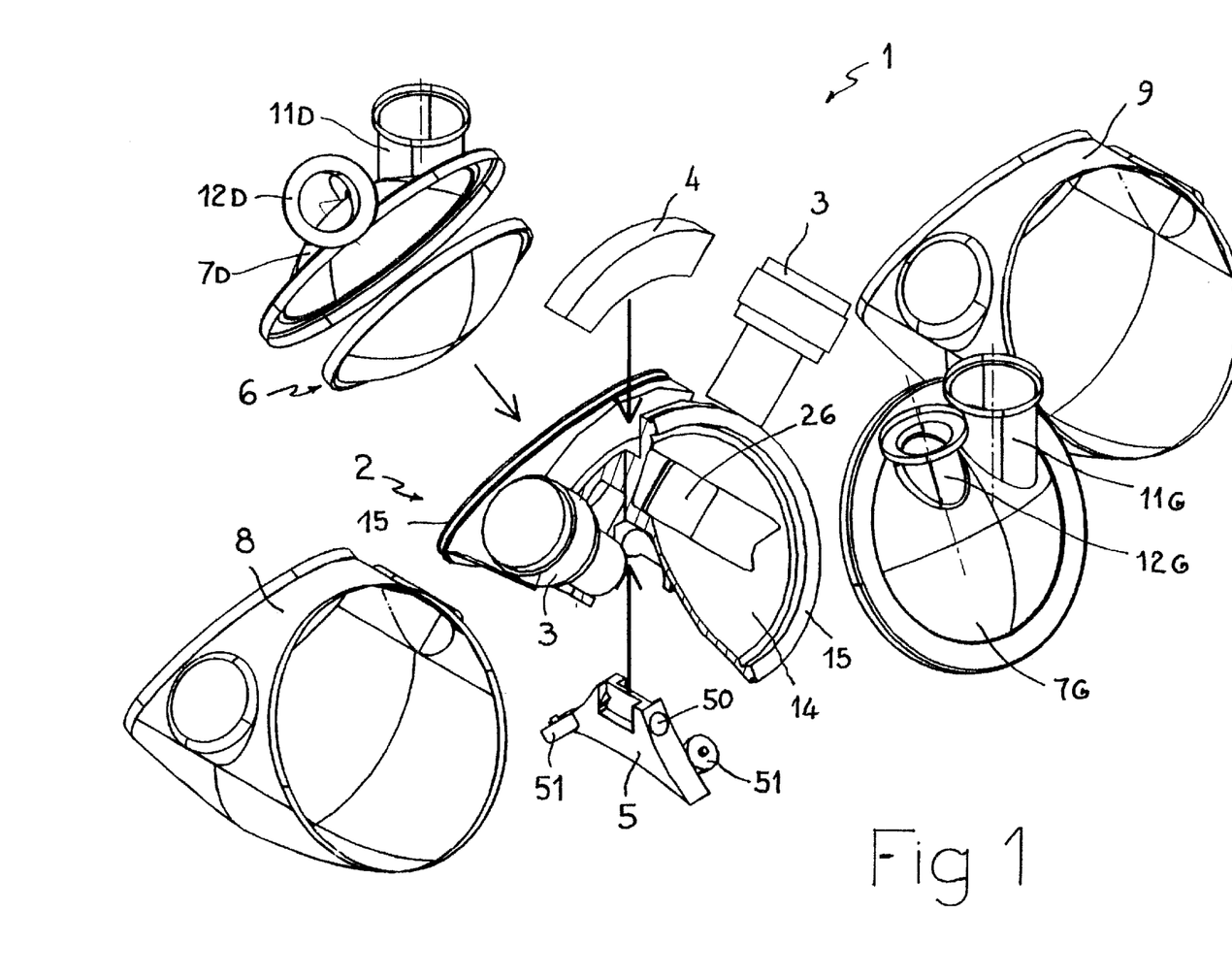
FIG. 1 is an exploded view of the different functional units of the artificial heart.

As shown in FIG. 1, the totally implantable artificial heart 1 comprises a central body 2 e.g. made of plastics material housing: two inclined motorized pump groups 3, the motor drive electronic circuit board 4 at the top portion, the control electronic circuit board 5 for the ventricular pressure and membrane position sensors at the bottom, on each side a membrane unit 6 and respective left 7G and right 7D ventricular caps fitted with blood ducts (here, "left" and "right" refer to the conventional terms for a human heart and are therefore reversed with respect to the diagrammatic representation). Around the assembled body 2 are inserted the supple reservoir bag 8 and the rigid body shell 9.

All the exterior surfaces of the fully assembled heart 1 (FIGS. 2 and 3) are made of titanium, a material known for its good hemocompatibility. The latter include the surfaces of the shell 9 and the ventricular caps 7G and 7D. The two-part shell 9 is roughly in the shape of an elbow sleeve whose two circular end sections are formed by the above curved ventricular caps 7G, 7D, inclined along dihedral planes with the angle towards the top.

Figure 2:
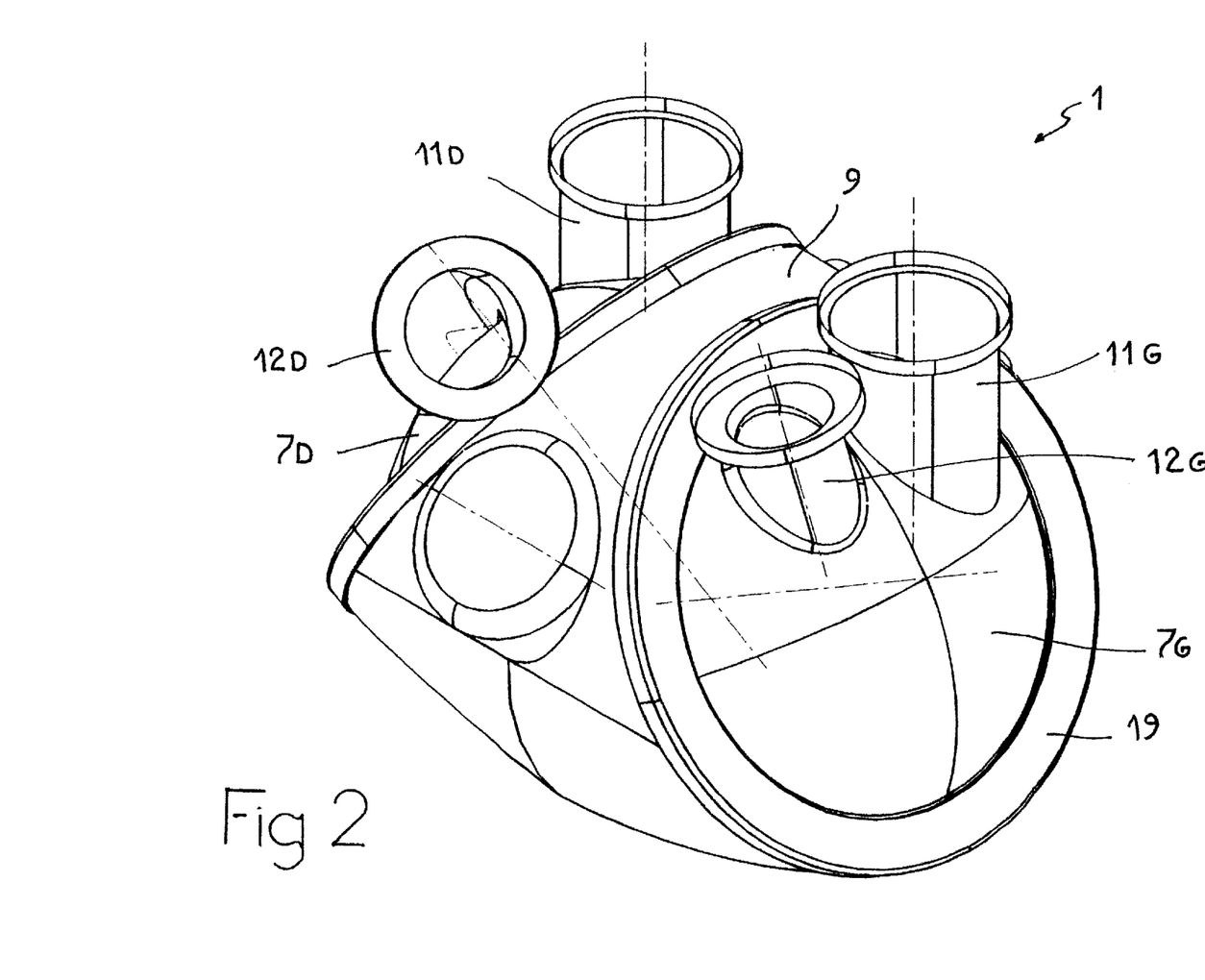
FIG. 2 is a perspective view of the assembled units.
Figure 3:
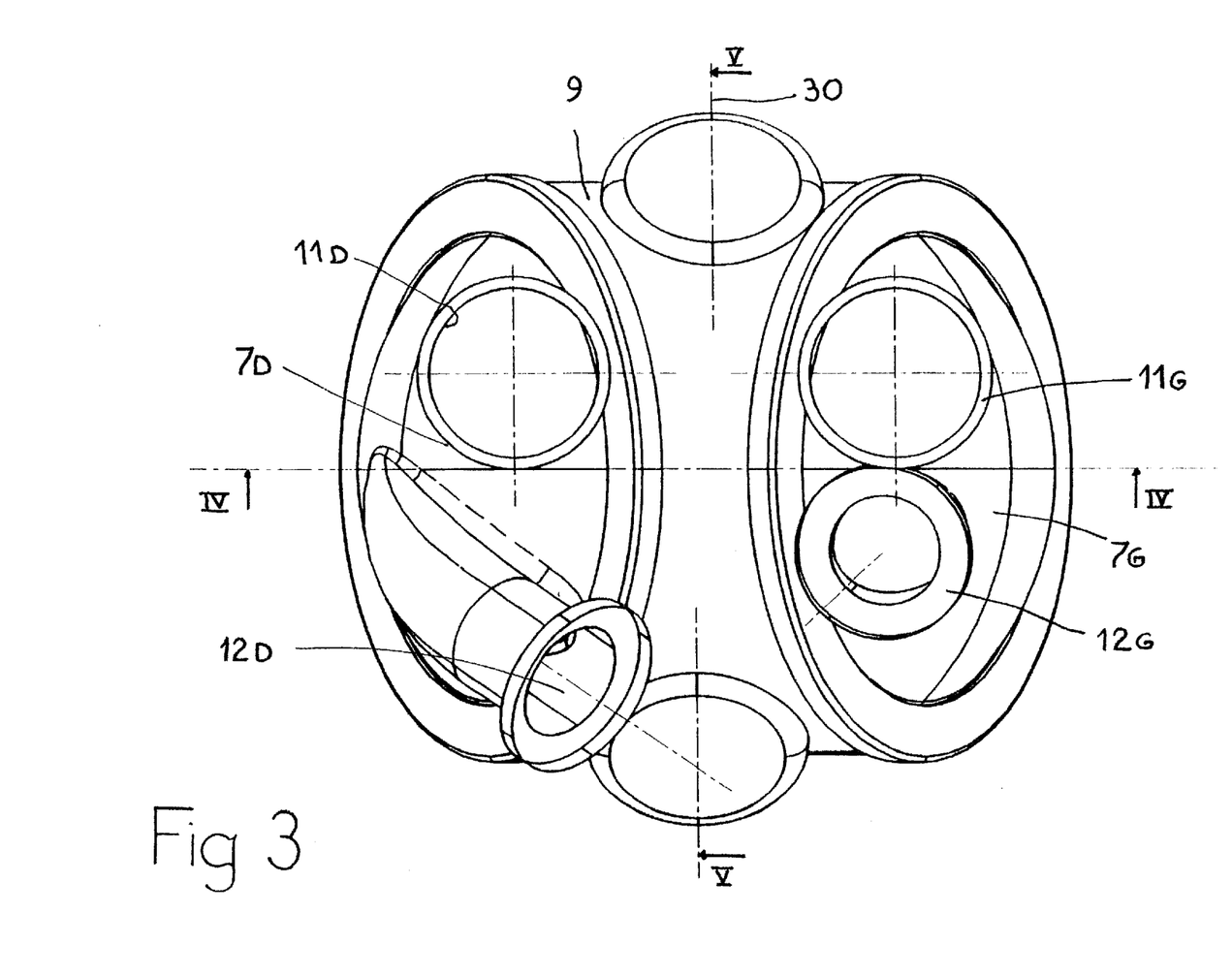
FIG. 3 is a plan view of the above assembly.

The dome-shaped portion of the left cap 7G comprises an admission tube 11G for connection to the left auricle and an evacuation tube 12G for connection to the aorta.

The dome-shaped portion of the right cap 7D comprises an admission tube 11G for connection to the right auricle and an evacuation tube 12D for connection to the pulmonary artery.

The different tubes 11 and 12—made of titanium—comprise inside their orifices the necessary valves known to the skilled person. They also comprise rims and connection flanges. Finally, their positioning (separation and inclination) is adapted to correspond as best as possible to the location of the natural organs to which they are to be connected.

The central body (FIGS. 1, 4, 5, 7, and 8) is made of a plastics material by machining or molding in the shape of a hub 13 which is substantially symmetrical with respect to the median vertical plane 30. The hub laterally defines two small cups 14 surrounded by circular edges 15 intended to receive the membrane units 6 and the rims of the ventricular caps 7G, 7D.

An internal shoulder 31 beneath the edge 15 serves to lodge the membrane units 6, whilst outside the edge 15 a peripheral groove 32 is provided to receive a sealing ring when fitting the coupling flanges 19. The top of the hub 13—which is the narrowest portion of the body 2 where the small cups 14 come closest together—is cleared at the center and forms a hollowed sector 33 for receiving the electric motor drive circuit board 4. The lower part of the hub—which is broader since the small cups 14 are spaced apart—also forms a housing 34 for the insertion of the control electronics circuit board 5. The hub 13 also integrates though-holes 35 for partially housing the motorized pumps 3. The holes 35 are substantially centered on the median plane 30 and from between them an angle advantageously in the region of 90°. A rectangular window 26 allows the inside of the hole 35 to communicate with the small cup 14 to which it is connected by means of an expansion 36 intended to gradually slow down the fluid.

Each membrane assembly 6 comprises a circular mounting device 16 in which are mounted the two supple membranes 17, 18 which are respectively mechanical (made of plastics material) and biological (in pericardium), as disclosed in document FR-A-2 625 903. The circular mounting device 16 lodges against the annular shoulder 31 of edge 15, and is blocked by the ventricular cap 7G, 7D and a flange 19. A sealing joint 20 is provided between the groove 32 of the hub 13 and the flange 19 fixing the cap.

Figure 4:
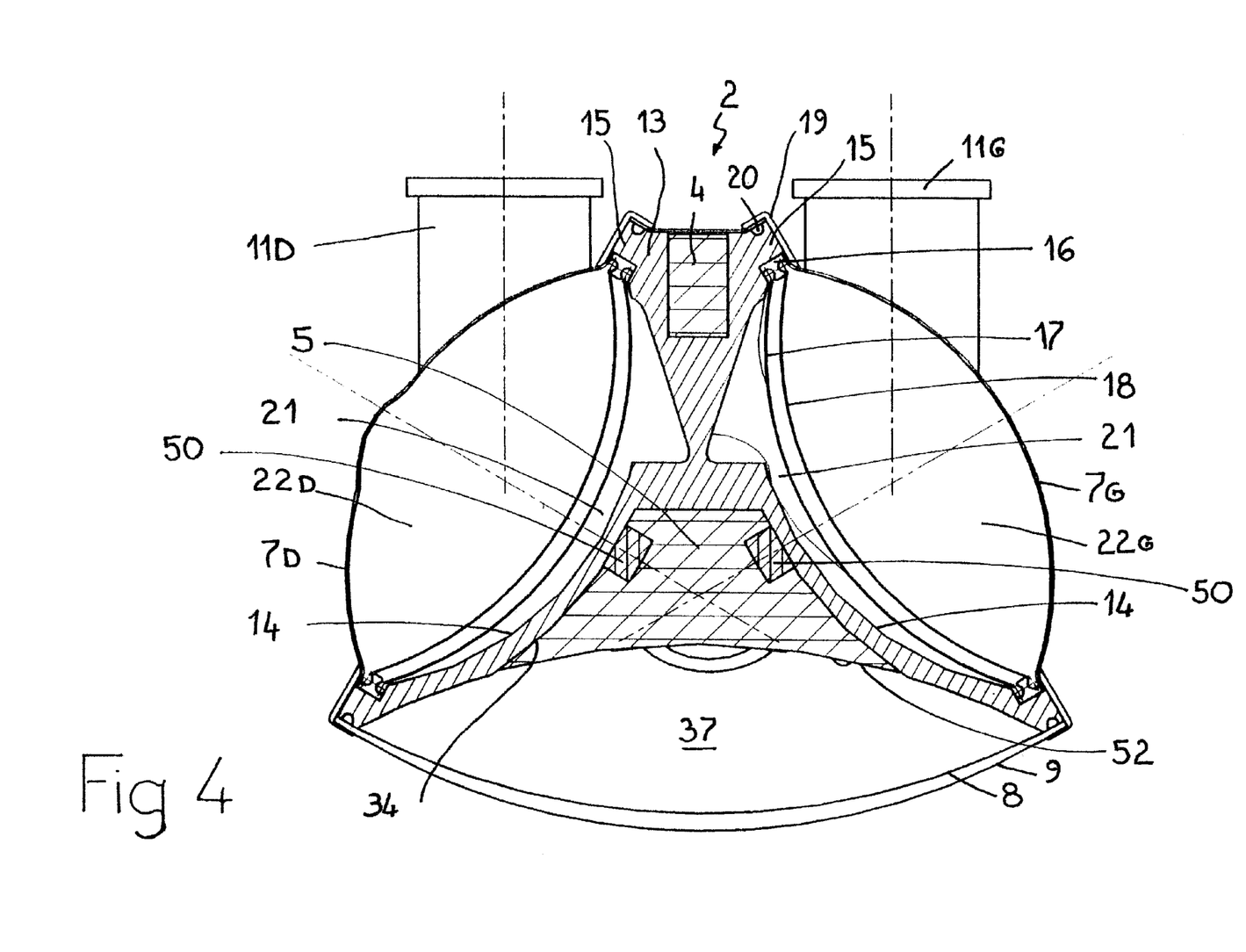
FIG. 4 is a central cross-sectional view along the line IV—IV of FIG. 3, parallel to the axes of the auricular orifices.

As shown in FIG. 4, the small cup 14 of the hub delimits an oil chamber 21 with the membrane 17, whilst the membrane 18 delimits with the cup 7G, 7D a blood chamber 22G, 22D corresponding respectively to the left and right ventricles of the heart, in fluid communication with pipes 11 and 12.

The membranes are actuated by the motorized pumps 3 housed on the hub 13 between the small cups 14 opposite the oil chambers.

Figure 5:
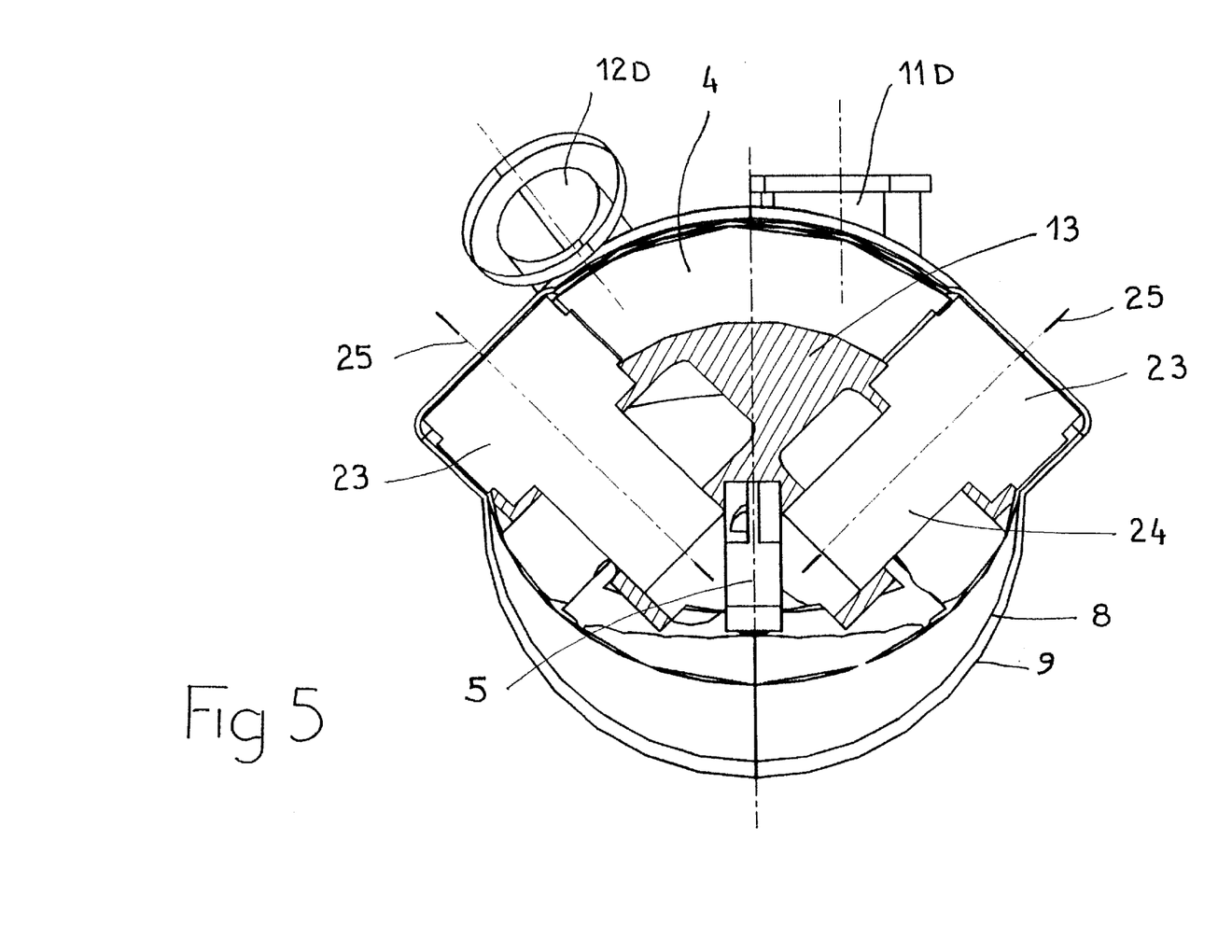
FIG. 5 is cross-sectional view along the line V—V of FIG. 3 passing through the motorized pump units.
Figure 6:
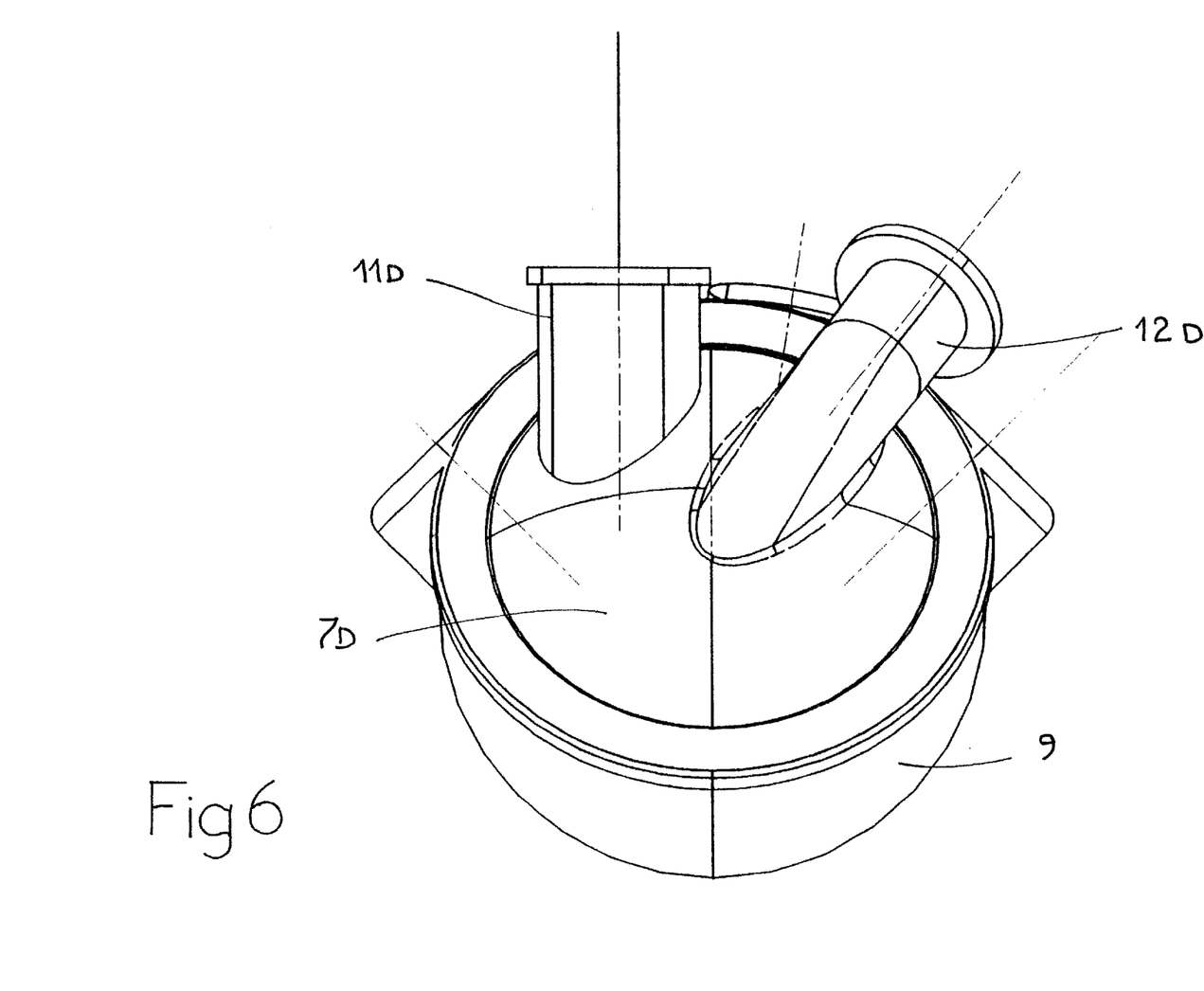
FIG. 6 is a left view of the heart shown in FIG. 3.
Figure 7:
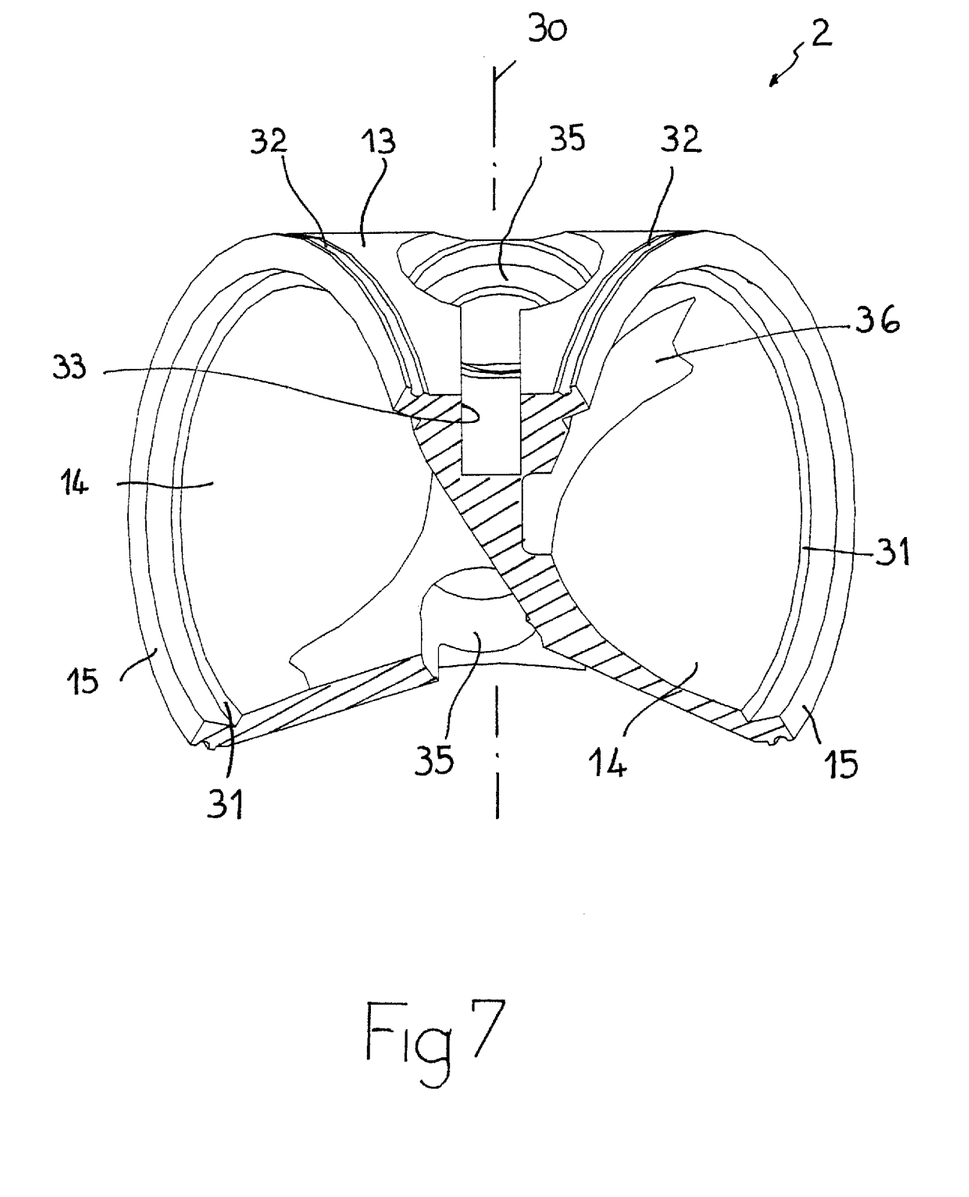
FIG. 7 is a plan view, with partial cutaway portions, of the central body.
Figure 8:
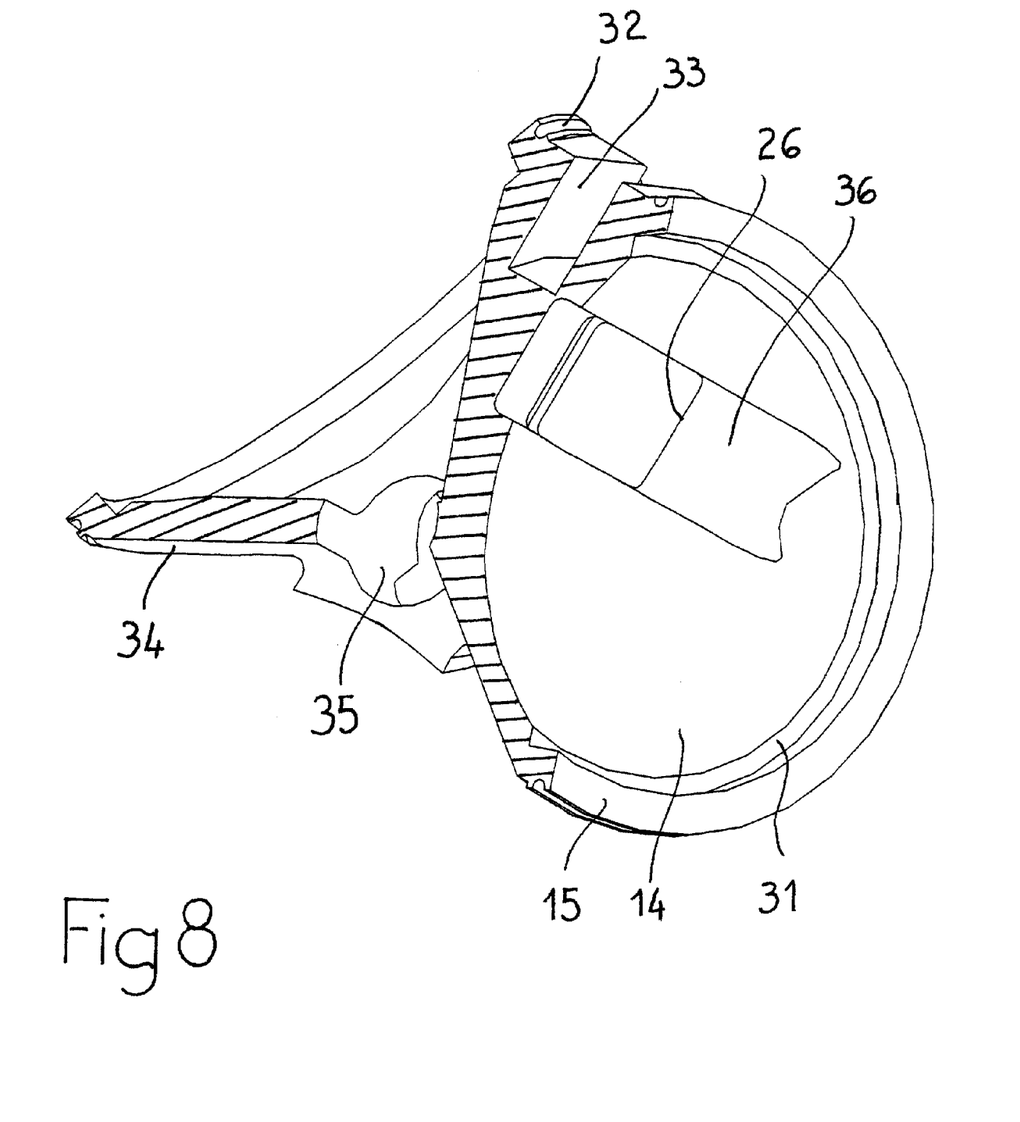
FIG. 8 is an axonometric perspective view of the central body shown in FIG. 7.

Each motorized pump 3 comprises a motor portion 23 and a pump portion 24 arranged on a common axis 25. The two axes 25 of the two motorized pumps are substantially in the median symmetry plane 30 of the hub 13, and form between them an angle which is advantageously in the region of 90°, as shown in FIG. 5.

Figure 9:
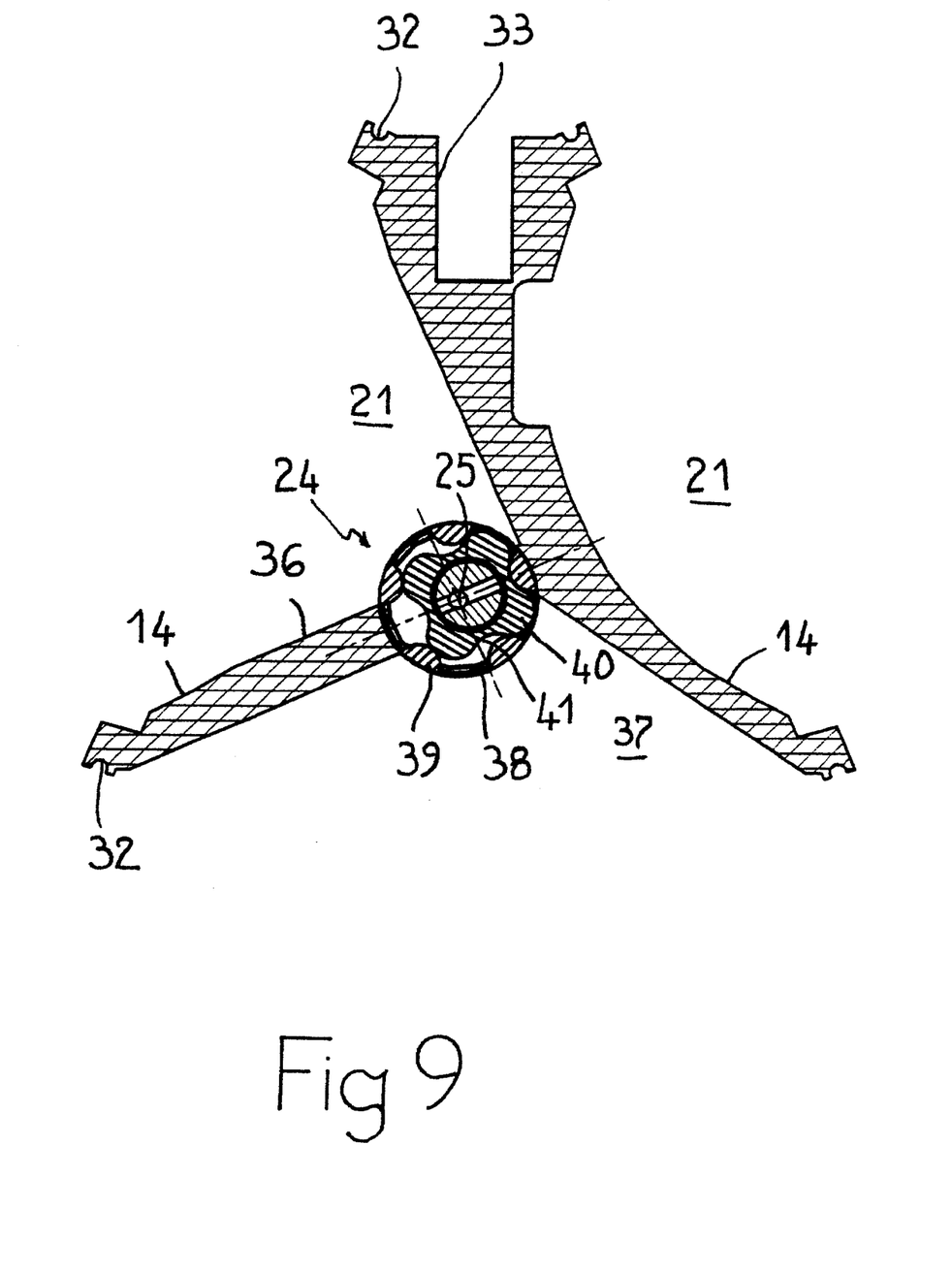
FIG. 9 is a detailed right-angular cross-sectional view of an actuator pump.

Pump 24 is a volumetric pump with internal gears and radial intake and outflow. Pump 24 communicates on one side with the actuating chamber 21 by means of a window 26 formed in the small cup 14 and on the other side with an internal space 37 filled with a transmission fluid (advantageously mineral or silicon oil), as shown in FIG. 9. This figure shows the outer crown 38 with an internal gearing composed of n lobes 39 in which engage n–1 lobes 40 of the internal eccentric element 41. The crown 38 rotates on axis 25 and a drive mechanism, known per se, is provided for the internal element 41. The lobes of the external crown 38 are sufficiently spaced apart to allow a large fluid passage in the radial direction, without excessive load losses.

Figure 10:
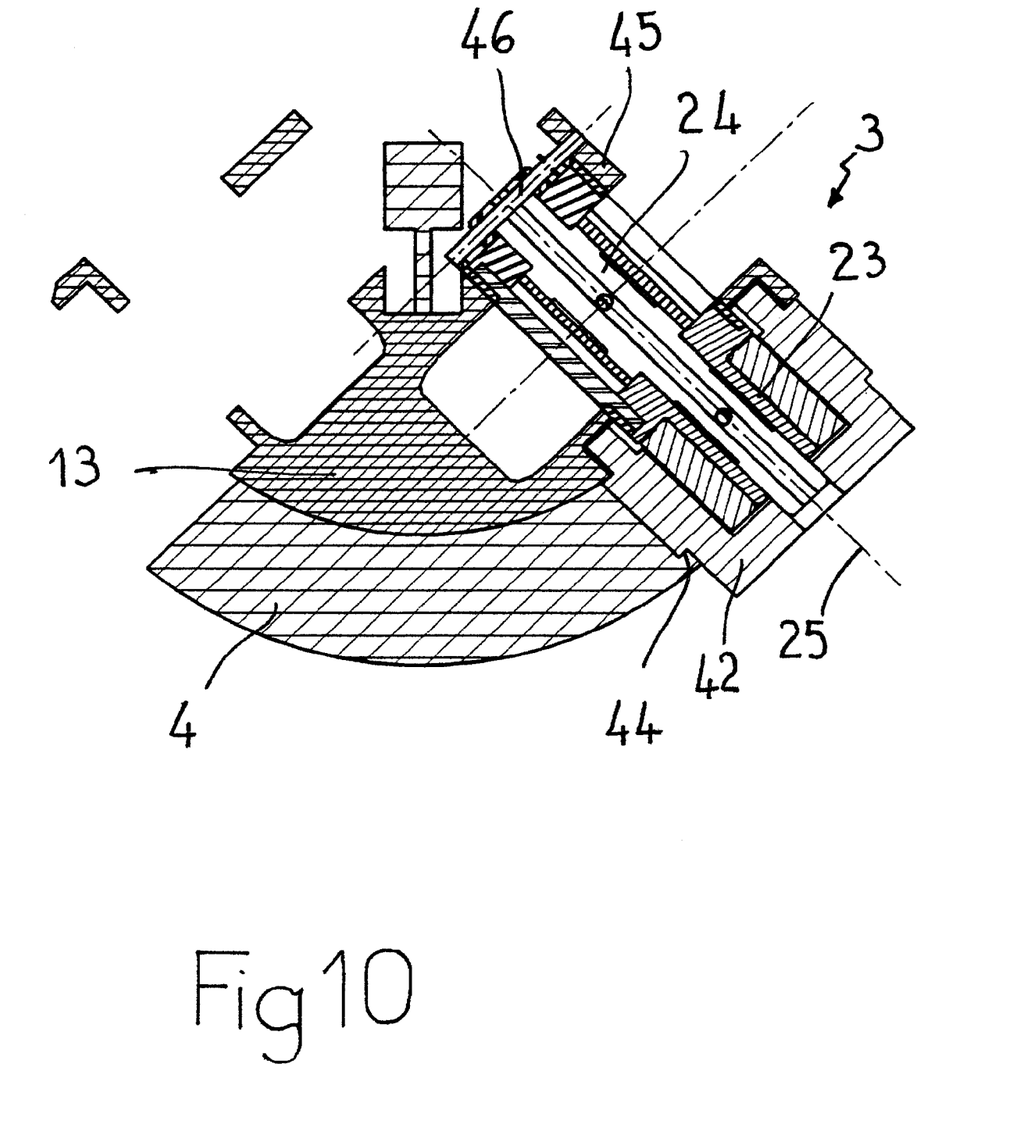
FIG. 10 is a detailed axial cross-sectional view of an actuating motorized pump group.

FIG. 10 shows the axial installation of the motorized pump unit 3 in the hub 13 of the central body. The stator 42 is stuck to the hub 13 and axially positioned by a shoulder portion 44 of the stator 42. The rotor of the motorized pump unit 24 is introduced into the stator 42 from the inside and is closed off with a lid 45 which is blocked by means of a locking pin 46.

The motors are brushless direct current motors whose drive electronics are contained in board 4.

The control electronics are grouped in the lower board 5. The latter also accommodates Hall effect sensors 50 which cooperate with a magnet placed on the magnetic membrane 17 to detect the position where it is close to the bottom of the small cup 14 (diastolic position where the biological chamber 22 has the maximum volume). This end of travel detection makes it possible to control the measured volume in a known manner directly by the sensors integrated in the volumetric pump, so as to recalibrate the measurement and eliminate drifts due to inherent leakages of the pump. Board 5 also supports oil pressure and blood pressure sensors 51.

As shown in FIG. 4, the profile of the internal surface 52 of the board 5 is made substantially symmetrical with that of the housing shell 9, at its lower portion, so as to give the supple bag 8 a neutral fiber of the same length (in the plane of the figure) when it adopts its minimum volume position (all the oil of the volume 37 is expulsed in one or the other of the oil chambers 21), and to minimize its flexing in that direction. Note that by virtue of the abutment provided by the above lower surface 52, the supple bag 8 does not risk being aspirated by the pumps of units 3 and that a strainer is not necessary.

The artificial heart according to the invention is assembled as follows. After manufacturing the hub 13 of the central body 2, the stator of motor 3 is stuck, and the rotors of the motorized pumps 24 are mounted as explained above. The pressure and position sensors are positioned, followed by the electronic boards 4 and 5, and the necessary connections are made. The reservoir bag 8 is slipped around the central body 2, after which the membrane units 6 are placed, followed by the caps 7 on each side of the body 2. The two-part housing shell is fixed around the assembly by two flanges. The drawings do not show the air vents provided in the body shell 9, nor the electrical connections joining the electronic boards 4 and 5 to an external power source.

What is claimed is:

1. A wholly implantable artificial heart of the type comprising within a single-piece module two independent ventricular chambers with movable membranes arranged in a V and each provided with two orifices oriented towards the top and equipped with a valve means respectively for the expulsion and admission of blood, each chamber having a variable volume by means of the movable membrane forming a wall of the chamber and hydraulically actuated by actuating fluid driven by an actuator comprising a motor and a volumetric pump;

wherein said ventricular chambers are arranged so as to form an upside down V, pointing toward the top, and between two of the branches of the V are arranged said actuators and the space for the actuating fluid.

2. Artificial heart according to claim 1, wherein the chambers include outside curved walls on which are disposed the expulsion and admission orifices.

3. Artificial heart of according to claim 1, wherein the actuators are arranged substantially in a zone of the median symmetry plane of the V formed by the chambers, the axes thereof forming approximately a right angle, and the motors being located outside of the right angle and the pumps inside said right angle.

4. Artificial heart according to claim 1, further comprising a central body supporting said actuators and defining two cups inclined in a V configuration the edge of which retains said movable membrane surmounted by said curved wall made of titanium, each cup forming with the membrane an actuating chamber supplied with oil by the actuators whose pump is interposed between the internal space of said chamber and an oil confinement space formed in and around the central body and limited by a supple bag reservoir, the assembly being enclosed in a rigid titanium body shell.

5. Artificial heart according to claim 4, wherein the central body comprises housings for receiving a motor drive electronic circuit board and a control and sensor electronic circuit board.

6. Artificial heart according to claim 4, wherein said central body is made of plastics material.

7. Artificial heart according to claim 5, wherein said central body is made of plastics material.

* * * * *